(12) United States Patent
Horne

(10) Patent No.: US 9,080,837 B2
(45) Date of Patent: Jul. 14, 2015

(54) FIREARM MULTI-PURPOSE TOOL

(71) Applicant: John Horne, Loa Alamos, NM (US)

(72) Inventor: John Horne, Loa Alamos, NM (US)

(*) Notice: Subject to any disclaimer, the term of this patent is extended or adjusted under 35 U.S.C. 154(b) by 0 days.

(21) Appl. No.: 14/305,689

(22) Filed: Jun. 16, 2014

(65) Prior Publication Data

US 2014/0290112 A1 Oct. 2, 2014

Related U.S. Application Data

(63) Continuation of application No. 13/199,163, filed on Aug. 22, 2011, now Pat. No. 8,171,825.

(51) Int. Cl.
*F41C 27/00* (2006.01)
*A61M 37/00* (2006.01)
*H02K 11/00* (2006.01)
*H02K 33/04* (2006.01)

(52) U.S. Cl.
CPC ............ *F41C 27/00* (2013.01); *A61M 37/0076* (2013.01); *H02K 11/0073* (2013.01); *H02K 33/04* (2013.01)

(58) Field of Classification Search
USPC .................................. 42/90, 106, 108; 7/118
See application file for complete search history.

(56) References Cited

U.S. PATENT DOCUMENTS

| 404,001 | A | * | 5/1889 | Heacock | 7/139 |
| 439,336 | A | * | 10/1890 | Zitlow | 81/437 |
| 5,204,483 | A | * | 4/1993 | Tellechea | 42/95 |
| 5,416,940 | A | * | 5/1995 | Bandera | 7/118 |
| 5,685,206 | A | * | 11/1997 | Ma | 81/77 |
| 5,845,354 | A | * | 12/1998 | Long et al. | 7/139 |
| 7,174,667 | B2 | * | 2/2007 | Connal | 42/108 |

* cited by examiner

*Primary Examiner* — Reginald Tillman, Jr.
(74) *Attorney, Agent, or Firm* — David O. Simmons

(57) ABSTRACT

A multi-purpose firearm servicing tool has an elongated tool body having a first end portion and a second end portion. A gas tube clamp is provided at a position between the first and second end portions of the elongated tool body. Opposing tube clamp surfaces of the gas tube clamp are selectively movable between a tube clamping configuration and a tube receiving configuration. A torque handle body has a tool body receiving cavity accessible through an opening at an end face at a first end portion thereof. The first and second tool body structures are stowable within the tool body receiving cavity. The torque handle body and the tool body each include respective means for allowing the tool body to be coupled to the torque handle body for allowing a rotational torque to be applied to the tool body through rotation of the torque handle body.

12 Claims, 5 Drawing Sheets

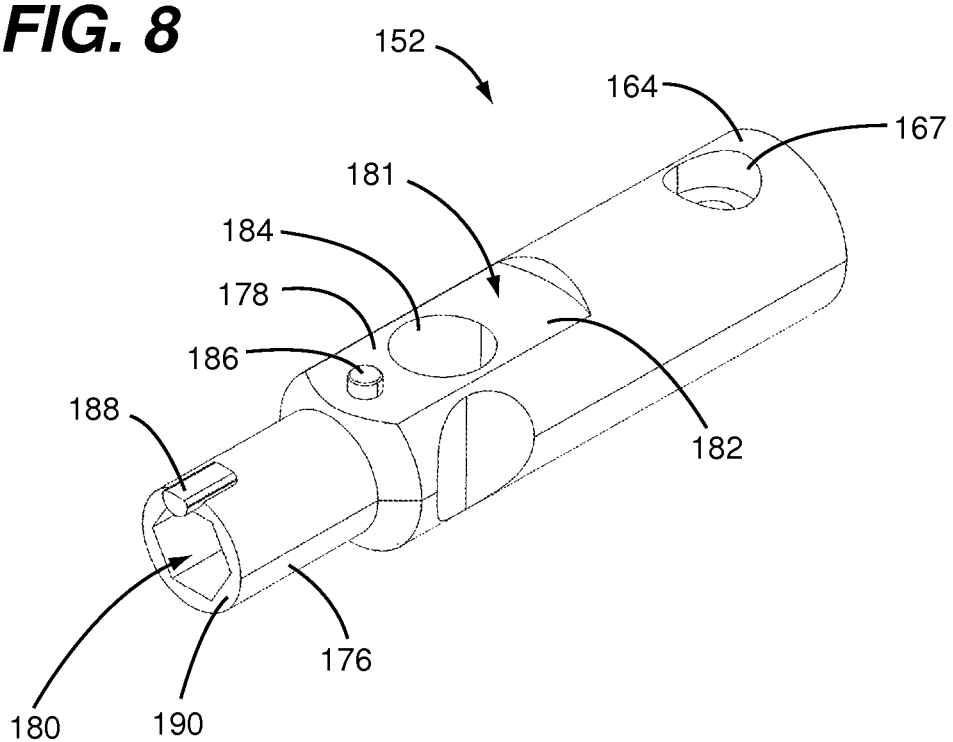

FIREARM MULTI-PURPOSE TOOL

FIELD OF THE DISCLOSURE

The disclosures made herein relate generally to firearms and, more particularly, to multi-purpose tools used for servicing firearms.

BACKGROUND

The proper and reliable operation of a firearm is of critical importance in combat, law enforcement, and civilian applications. In cases where the firearm is not properly serviced (e.g., maintained and/or repaired), the firearm can be subject to malfunctions, poor discharge performance, and/or poor accuracy and aiming performance. Of particular interest with respect to the disclosures made herein, a gas-operated automatic (e.g., fully automatic and/or semi-automatic) rifle such as, for example, a rifle in the AR15/M16/M4 family, a rifle in the AR-10/SR-25 family, etc is susceptible to malfunction and/or poor discharge and cycling performance due to build-up of combustion gas deposits and requires certain adjustments for maintaining precision aiming performance. As such, it is beneficial, if not necessary, to perform service operations such as, for example, field stripping and cleaning of such a rifle's components, adjusting its front and/or rear sights, and the like.

U.S. Pat. No. 4,817,321 to Clement teaches a multipurpose tool for a cap lock muzzle loading firearm, which does not provide necessary utility for properly servicing a gas-operated automatic rifle. US published patent application no. 2010/0325933 to Huang teaches a multifunction tool kit for firearm maintenance that is particularly configured for use with the M14/M1A family of rifles, but lacks many of the tool elements needed for essential aspects of servicing a gas-operated automatic rifle to maintain its proper and reliable operation. US published patent application No. 2009/0199345 to Morgan and U.S. Pat. No. 7637049 to Samson each teach respective combination tool that is particularly configured for use with the M16/M4 family of rifles and that contains numerous attached implements that are frequently used to maintain such firearms in working condition. But, as is the case with the multifunction tool kit of Huang, the combination tools of both Morgan and Samson each lack many of the tool elements needed for essential aspects of servicing a gas-operated automatic rifle to maintain its proper and reliable operation.

Accordingly, a multi-purpose tool having tool elements needed for essential aspects of servicing a gas-operated automatic rifle to maintain its proper and reliable operation would be useful and desirable.

SUMMARY OF THE DISCLOSURE

Embodiments of the present invention relate to a multi-purpose tool having tool elements needed for servicing a gas-energized automatic firearm. Such servicing is important to maintaining the proper and reliable operation of the firearm. Accordingly, in preferred embodiments of the present invention, the multi-purpose tool has tool elements necessary for performing certain essential aspects for servicing a gas-operated (e.g., gas-energized gas-driven) automatic rifle.

In one embodiment of the present invention, a multi-purpose firearm servicing tool comprises a tool body and a plurality of tool elements. The tool body has a first end portion and a second end portion. A longitudinal centerline axis of the tool body extends through the first and second end portions of the tool body. The plurality of tool elements are each integral with a side face of the tool body at a respective position between the first and second end portions of the tool body. Each one of the tool elements provides a respective firearm servicing functionality.

In another embodiment of the present invention, a multi-purpose firearm servicing tool comprises a tool body, a gas tube clamp, and a torque handle body. The tool body includes a first tool body structure and a second tool body structure. The first tool body structure has a first threaded tool body interface at a first end portion thereof extending along a longitudinal centerline axis thereof The second tool body structure has a second threaded tool body structure interface at a first end portion thereof extending along a longitudinal centerline axis thereof The second threaded tool body interface is threadedly engaged with the first threaded tool body interface for causing the second tool body structure to be longitudinally displaced with respect to the first tool body structure in response to relative rotational displacement therebetween. The gas tube clamp is positioned between the first tool body structure and the second tool body structure. Opposing tube clamp surfaces of the gas tube clamp are selectively movable between a tube clamping configuration and a tube receiving configuration. The torque handle body has a tool body receiving cavity accessible through an opening at an end face at a first end portion thereof The first and second tool body structures are stowable within the tool body receiving cavity. The torque handle body and the tool body each include respective means for allowing the tool body to be coupled to the torque handle body for allowing a rotational torque to be applied to the tool body through rotation of the torque handle body.

In another embodiment of the present invention, a multi-purpose firearm servicing tool comprises an elongated tool, a gas tube clamp, and a pin. The gas tube clamp is at a position between the first and second end portions of the elongated tool body. Opposing tube clamp surfaces of the gas tube clamp are selectively movable between a tube clamping configuration and a tube receiving configuration. A pin is fixedly attached to the tool body at the first end portion thereof.

These and other objects, embodiments, advantages and/or distinctions of the present invention will become readily apparent upon further review of the following specification, associated drawings and appended claims.

BRIEF DESCRIPTION OF THE DRAWINGS

FIG. 8 is a perspective view of a second tool body structure of the main tool shown in FIG. 6.

DETAILED DESCRIPTION OF THE DRAWING FIGURES

Figure 1:
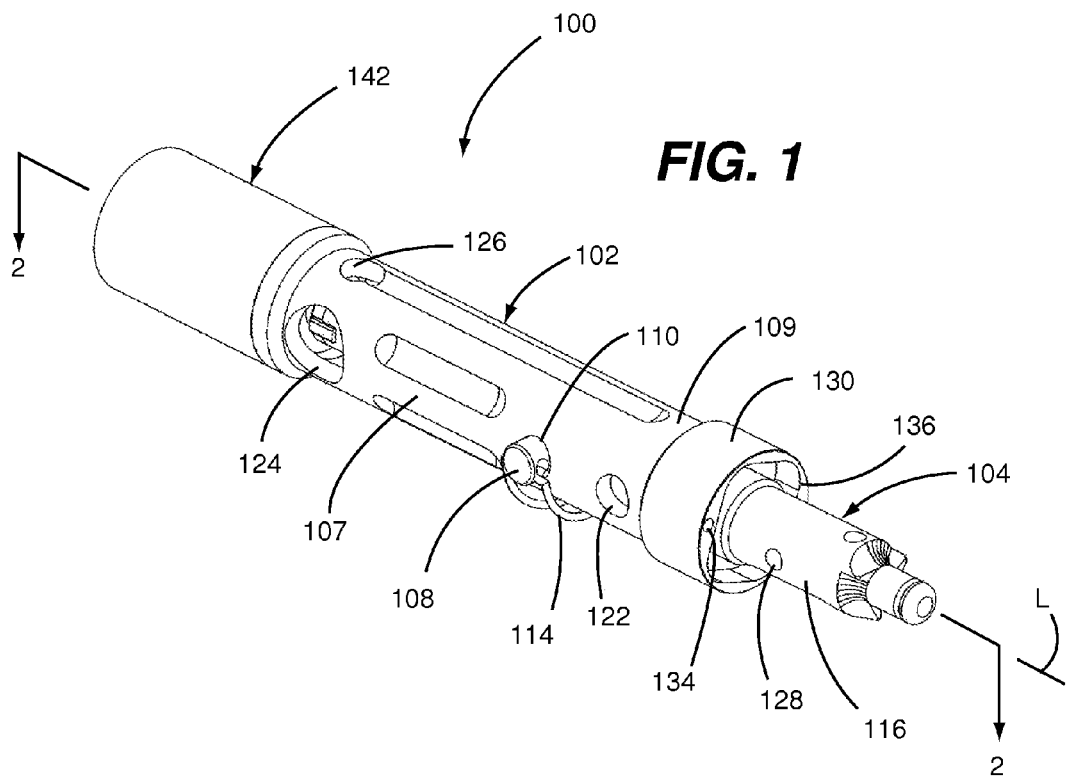
FIG. 1 is a perspective view showing a multi-purpose tool configured in accordance with an embodiment of the present invention.
Figure 2:
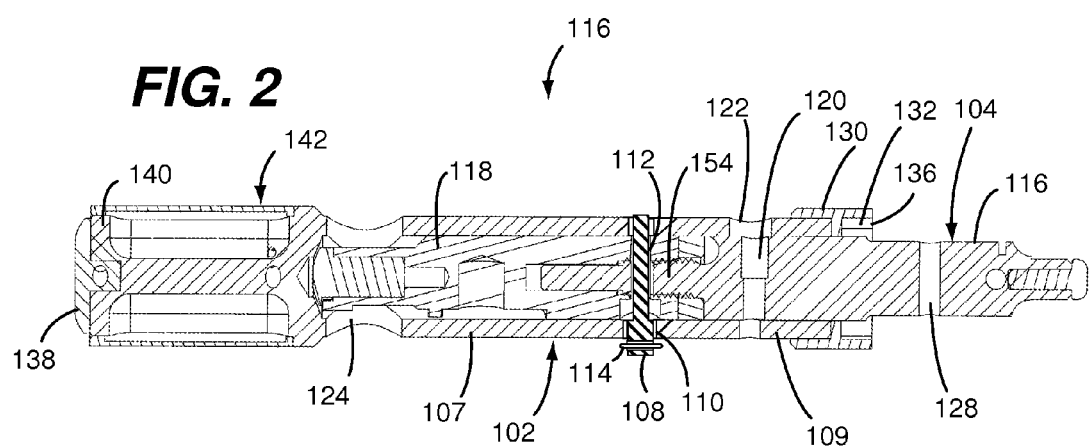
FIG. 2 is a cross-sectional view taken along the line 2-2 in FIG. 1.
Figure 3:
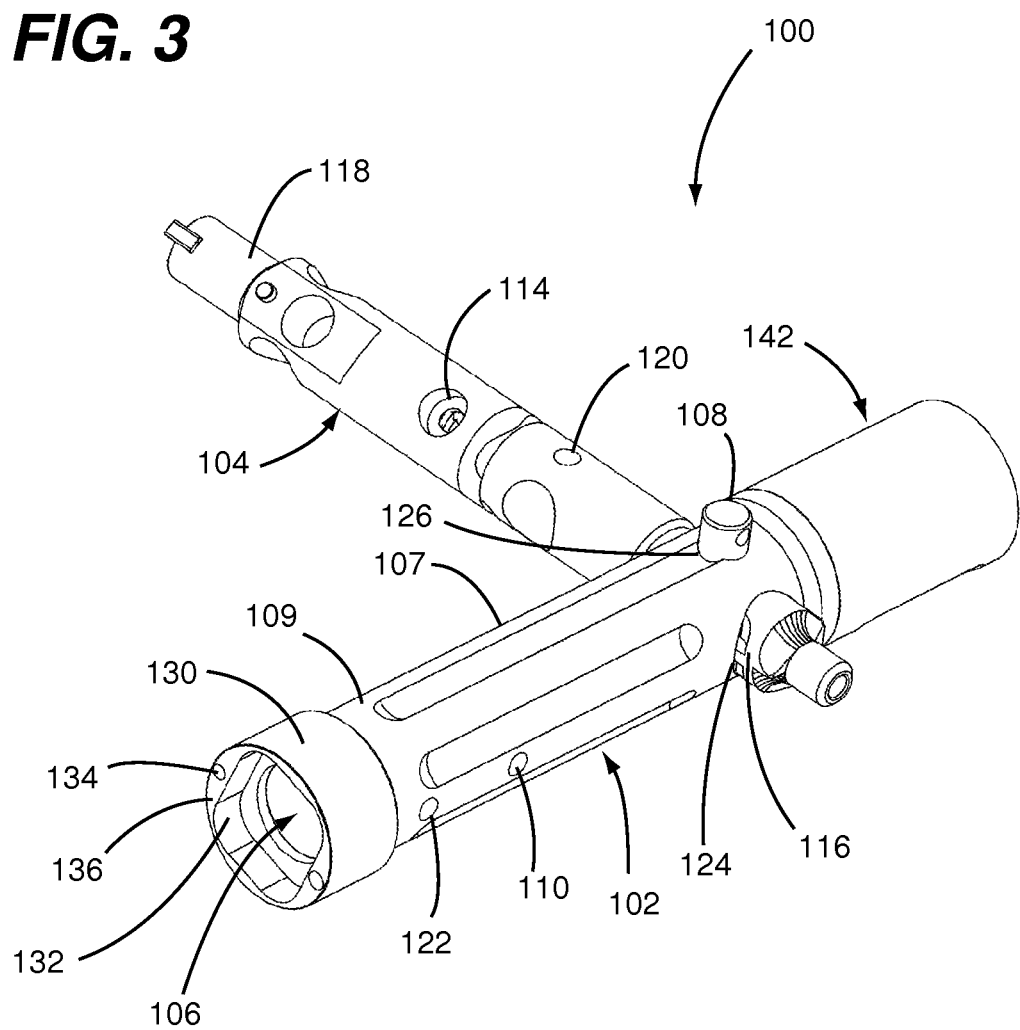
FIG. 3 is a perspective view showing the multi-purpose tool of FIG. 1 in a tee handle configuration.

Referring to FIGS. 1-3, a multi-purpose firearm servicing tool (i.e., tool 100) configured in accordance with the present invention is shown. The tool 100 includes tool elements needed for performing a multitude of service operations on a gas-energized automatic (e.g., fully automatic or semi-automatic) firearm. Such servicing is important to maintaining the proper and reliable operation of the firearm. To this end, the tool 100 has tool elements necessary for performing certain essential aspects for servicing a gas-operated rifle. However, in view of the disclosures made herein, a skilled person will appreciate that a tool configured in accordance with the present invention can be configured for use with firearms that are of a design other than gas-operated, configured for firearms other than rifles, and/or configured for performing additional service operations.

The tool 100 includes a torque handle 102 and a main tool 104. As will be discussed below, the torque handle 102 and the main tool 104 each include various tool elements needed for performing the multitude of service operations on a gas-energized automatic firearm. Furthermore, as will also be discussed below, the torque handle 102 and the main tool 104 can be engaged with each other in a number of configurations for providing combined utility.

Referring to FIGS. 1 and 2, the main tool 104 can be mounted within a central passage 106 (see FIG. 3) of a torque handle body 107 of the torque handle 102. In this regard, the central passage 106 can also be referred to as a tool body receiving passage. The central passage 106 is assessable at a first end portion 109 of the torque handle body 107. A cross pin 108 is jointly engaged within a first cross pin passage 110 of the torque handle 102 and a first cross pin passage 112 of the main tool 104 for retaining the main tool 104 within the central passage 106 of the torque handle 102. A catch spring 114 is selectively engagable between the torque handle 102 and the cross pin 108 for securing the cross pin 108 in place. In this mounted configuration, the torque handle 102 and the main tool 104 jointly provide for tool functionalities along or about a longitudinal centerline axis L of the main tool 104. Such a longitudinal coupling of the torque handle 102 and the main tool 104 is referred to herein as an in-line tool handle configuration.

Still referring to FIGS. 1 and 2, the main tool 104 is secured in the torque handle 102 with its first end portion 116 protruding from within the central passage 106 of the torque handle 102. In this configuration, tool elements exposed outside of the central passage 106 of the torque handle 102 at the first end portion 116 can be used for performing respective service operations. Alternatively, the main tool 104 can also be secured in the torque handle 102 with its second end portion 118 protruding from within the central passage 106 of the torque handle 102 thereby allowing tool elements exposed outside of the central passage 106 of the torque handle 102 at the second end portion 118 of the main tool 104 to be used for performing respective service operations. In this alternate mounted configuration, the cross pin 108 would be jointly engaged within the first cross pin passage 110 of the torque handle 102 and a second cross pin passage 120 of the main tool 104 for retaining the main tool 104 within the central passage 106 of the torque handle 102. As shown, in FIG. 2, it is disclosed herein that the torque handle 102 can include one or more other cross pin passages besides the first cross pin passage 110 (e.g., the second cross pin passage 122 of the torque handle 102).

As shown in FIG. 3, the main tool 104 can be mounted within a lateral passage 124 of the torque handle 102. The cross pin 108 is jointly engaged within a third cross pin passage 126 of the torque handle 102 and a third cross pin passage 128 of the main tool 104 (shown in FIGS. 1 and 2) for retaining the main tool 104 within the lateral passage 124 of the torque handle 102. In this mounted configuration, the torque handle 102 and the main tool 104 jointly provide for enhanced rotational leverage of torque handle 102 through force application on the main tool 104 and for enhanced rotational leverage of the main tool 104 through force application on the torque handle 102. Such a lateral coupling of the torque handle 102 and the main tool 104 is referred to herein as a Tee handle tool configuration.

Figure 4:
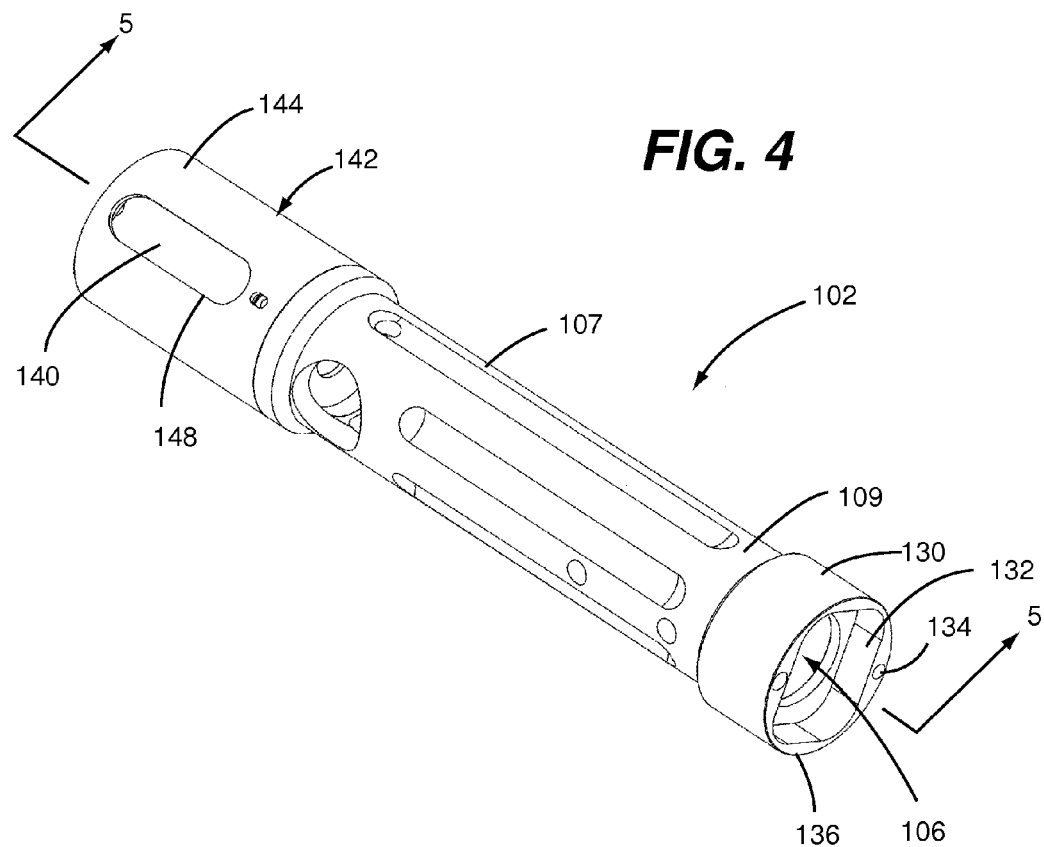
FIG. 4 is a perspective view of a torque handle of the multi-purpose tool of FIG. 1.
Figure 5:
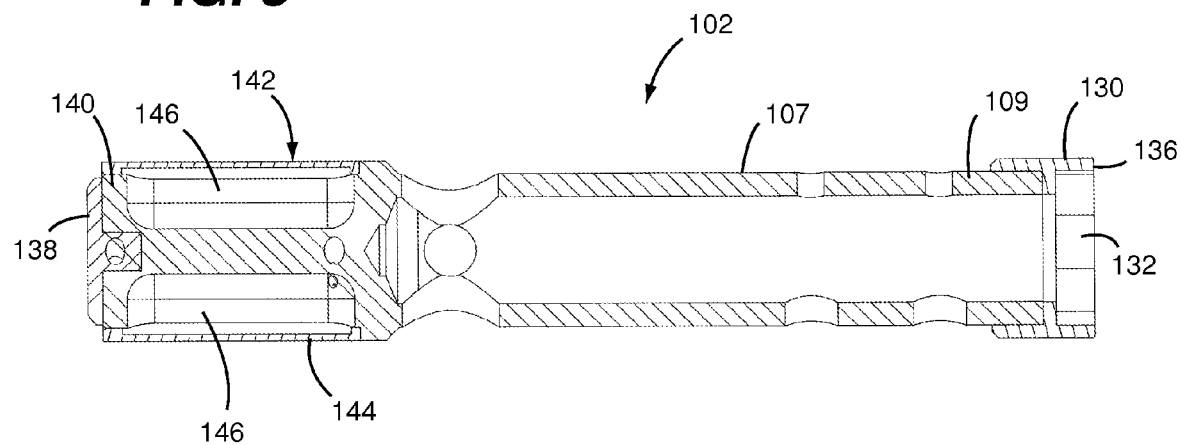
FIG. 5 is a cross-sectional view taken along the line 5-5 in FIG. 1.

Referring to FIGS. 3-5, the torque handle 102 is configured for providing a plurality of respective firearm servicing operations. A buffer tube nut receiving socket 130 is provided at the first end portion 109 of the torque handle body 107. The buffer tube nut receiving socket 130 can be an integrally formed portion of the torque handle body 107 or can be a separately formed structure that is permanently or removably attached to the torque handle body 107. The buffer tube nut receiving socket 130 include a buffer tube receiving recess 132 within which a mating nut of the buffer tube can be engaged, thereby providing a means for installing or removing the buffer tube of a firearm. Preferably, the torque handle 102 and the main tool 104 are coupled in the Tee handle configuration when loosening and tightening the buffer tube to provide enhanced leverage.

A plurality of pin starter recesses 134 (e.g., clearance holes) can be provided in an end face 134 of the buffer tube nut receiving socket 128. Each one of the pin starter recesses 134 can be diametrically sized for receiving a pin (e.g., a roll pin) of a respective diameter. Two common diameters for roll pins as used in firearms are nominally 0.078" and 0.093". Through insertion of a pin into a corresponding one of the pin starter recesses 134, the torque handle 102 can be used as a pin-driving implement. Pin driving force can be applied through impact applied on a strike face 138 at a second end portion 140 of the torque handle body 107 (shown in FIG. 5). In a preferred embodiment, the strike face 138 is made of H13 tool steel hardened to 50+RC.

Referring to FIGS. 4 and 5, a bit receiving structure 142 is provided at a second end portion 140 of the torque handle body 107. The bit receiving structure 142 includes a retention gate 144 that is rotatably mounted on the second end portion 140 of the torque handle body 107. A plurality of bit receiving pockets 146 are provides within a side face of the torque handle body 104 under the retention gate 144. Rotation of the retention gate 144 provides for selective access of contents of each one of the bit receiving pockets 146 through a pocket access gate (i.e., opening) 148 in the retention gate 144. Examples of contents of the bit receiving pockets 146 include, but are not limited to, driver bits (e.g., screw driving bits, hex socket bits, and other fastener engaging implements), spare firearm components (e.g., trigger pin), punches, and the like. Means such as, for example, a spring biased detent arrangement can be used for providing position positioning of the retention gate 144 relative to the bit receiving pockets 146.

Figure 6:
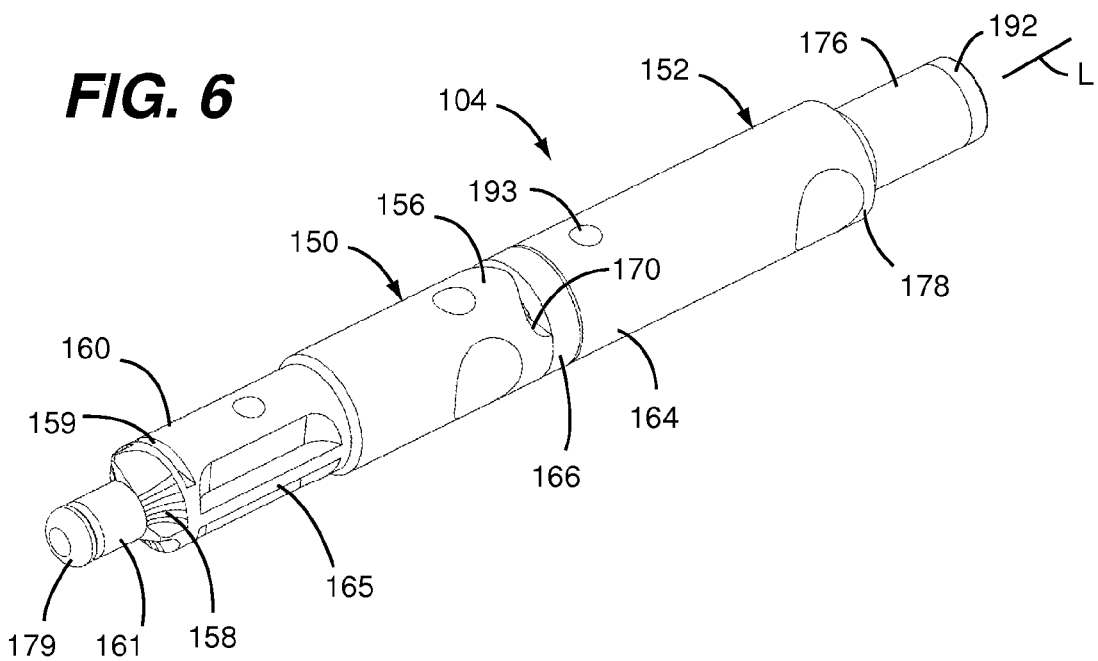
FIG. 6 is a perspective view of a main tool of the multi-purpose tool of FIG. 1.
Figure 7:
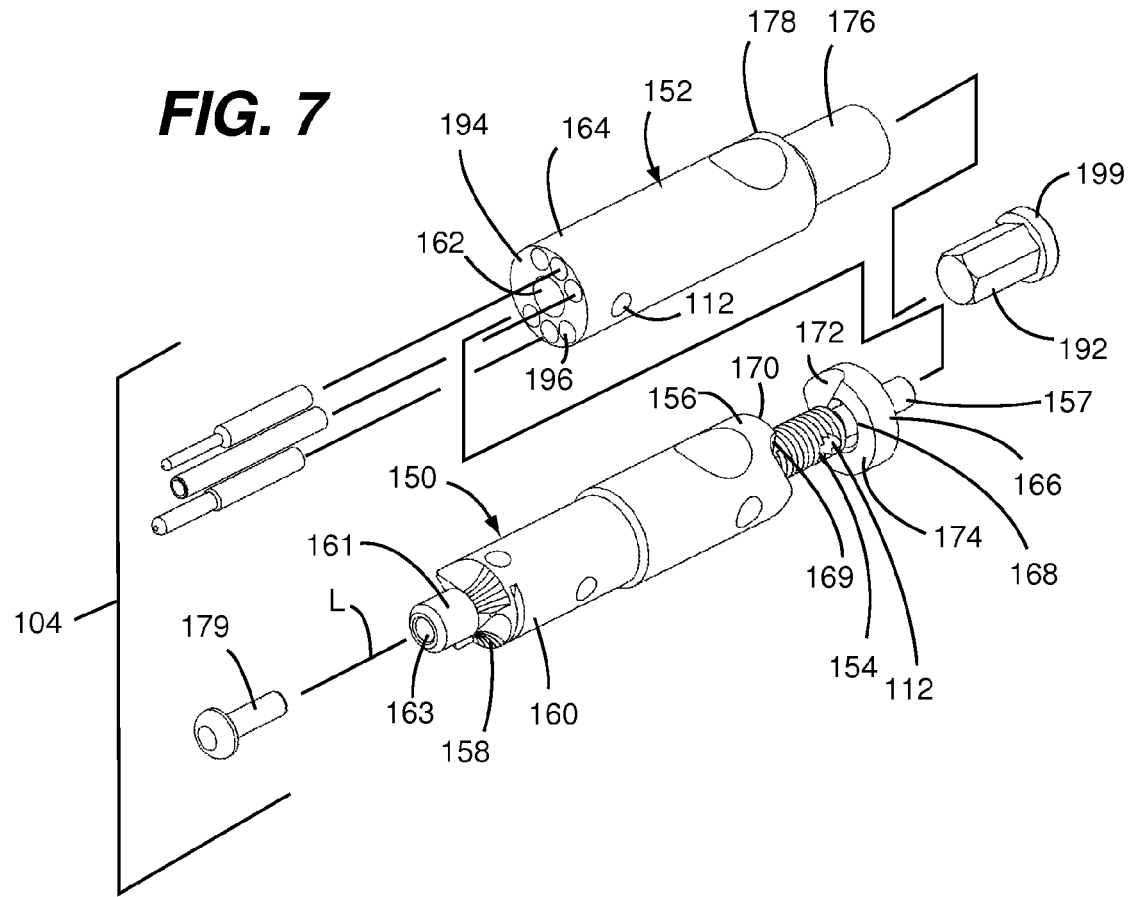
FIG. 7 is an exploded view of the main tool shown in FIG. 6.

Referring now to FIGS. 6-8, the main tool 104 includes a first tool body structure 150 and a second tool body structure 152. The first tool body structure 150 has a first threaded tool body interface 154 at its first end portion 156 extending along the longitudinal centerline axis L of the main tool 104. The second tool body structure 152 has a second threaded tool body structure interface 162 at its first end portion 164 extending along the longitudinal centerline axis L of the main tool body 104. A plurality of deposit scraping structures 158 are positioned at the second end portion 160 of the first tool body structure 150 around the longitudinal centerline axis L of the main tool 104. In a preferred embodiment, the deposit scrapping structures 158 are in the form of 3 sets of scraping flutes machined into the second end portion 160 of the first tool body structure 150 at approximately 120-degree spacing. These flutes can be used to scrape carbon build up from the bottom of a counter bore in a bolt carrier by inserting the second end portion 160 within the counter bore of the bolt carrier and causing relative rotation therebetween. An alignment boss 157 (shown in FIG. 6), preferably about 0.155 in diameter, extends from the first threaded tool body interface 154 along the longitudinal centerline axis of the main tool 104. The alignment boss 157 can be used for tasks such as, for example, aligning trigger group parts to aid in their assembly. A slot 159, preferably about 0.055" wide, can be provided in a side face of the first tool body structure 150 at its second end portion 160 for purposes such as, for example, straightening and repairing a feed lips on a standard military magazine.

A thumb screw slot engaging tool element 165 (FIG. 6) is integral with a side face of the first tool body structure 150. In a preferred embodiment, the thumb screw slot engaging tool element 165 is configured as an elongated beam having a thickness of about 0.070". A boss 161 (FIGS. 6 and 7), preferably about 0.25" in diameter, is provided at the second end portion 160 of the first tool body structure 150. The boss 161 can be used for tasks such as, for example, pressing out tight receiver push pins and also guiding the first end portion 160 when disposed within a mating hole within the end of a bolt carrier. The boss 161 has a central passage 163, preferably about 0.125" in diameter, that is used for accepting various implements such as drive punches. The depth of the central passage 163 of the boss 161 can be less than a length of a corresponding punch engaged therein for allowing the main tool 104 to be used as a slide hammer for impacting the punch. A roll pin set/index pin 179 can be removably mounted within the central passage 163 of the boss 161. The roll pin set/index pin 179 is used as a "safe" surface to finish setting roll pins in place. It has a shallow convex radius on its end surface that reduces damage to alloy receivers like that on firearms such as, for example, the M-16 rifle and AR-15 rifle.

The second threaded tool body interface 162 is threadedly engaged with the first threaded tool body interface 154 for causing the second tool body structure 152 to be longitudinally displaced with respect to the first tool body structure 150 in response to relative rotational displacement therebetween. As shown in FIG. 7, the first threaded tool body interface 154 is a threaded protrusion (e.g., threaded stud) and the second threaded tool body interface 162 is a threaded passage that is configured for having the threaded protrusion threadedly engaged therewith. It is disclosed herein that the threaded tool body interfaces of the first and second tool body structures can be implemented in the opposite relationship (i.e., threaded protrusion on the second tool body structure and threaded passage within the first tool body structure). It is also disclosed herein that the present invention is not unnecessarily limited to any particular configuration of tool body interface.

The roll pin set/ index pin 165 can also be used as a locking pin to allow the main tool 104 to be used as a screwdriver to remove and replace treaded fasteners (e.g., screws). To this end, the roll pin set/ index pin 165 is positioned within a counter bore passage 167 of the second tool body structure 152, thereby engaging a mating aligned passage of the first tool body structure 150 for inhibiting relative rotation between the two tool body structures. The main tool can be combined with the torque handle in the Tee handle tool configuration discussed above to add further leverage and utility Referring to FIGS. 6 and 7, a gas tube jaw 166 is disposed between the first tool body structure 150 and the second tool body structure 152. The first threaded tool body interface 154 extends through a central passage 168 of the gas tube jaw 166.

A contoured portion 169 of an end face 170 of the first tool body structure 150 and a gas tube engaging face 172 of the gas tube jaw 166 jointly define a gas tube clamp in which a gas tube of a firearm can be clamped as the first tool body structure 150 is longitudinally displaced toward the second tool body structure 152 through relative rotational displacement therebetween. Preferably, the contoured portion 169 of the end face 170 of the first tool body structure 150 and the gas tube engaging face 172 of the gas tube jaw 166 each are shaped to enhance contact area engagement with the gas tube (e.g., a concave saddle shape). As shown, the end face 170 of the first tool body structure 150 and a mating end face 174 of the gas tube jaw 166 each have a generally flat portion extending substantially perpendicular to the longitudinal axis L of the main tool body 102. Furthermore, mating end faces of the gas tube jaw 166 and the second tool body structure 152 are each generally flat and extend substantially perpendicular to the longitudinal axis L of the main tool body 102. It is disclosed herein that the relationship of the gas tube jaw 166 with respect to the first and second tool body structures can be reversed such that the gas tube clamp is defined between surfaces of the gas tube jaw 166 and the second tool body structure 152.

Still referring to FIGS. 6-8, the second tool body structure 152 includes a bit engaging socket 176 at its second end portion 178. The bit engaging socket 176 is centered on the longitudinal centerline axis L of the main tool body 104. The bit engaging socket 176 includes a bit receiving passage 180 therein. In a preferred embodiment, walls defining the bit receiving passage 180 are configured such that the bit receiving passage 180 has a hexagonal cross-sectional shape. A rear sight windage wheel rotating tool element 181 is integral with a side face of the second tool body structure 152. In a preferred embodiment, the windage wheel rotating tool element 181 includes a flat surface 182 on the side face of the second tool body structure, a cavity 184 within the flat surface 182, and a drive lug 186 extending from the flat surface 182.

A pin 188 is fixedly attached to the second tool body 152 at the second end portion 178 thereof. The pin 188 protrudes beyond an end face 190 of the bit engaging socket 176. In a preferred embodiment, the pin 188 is in the form of an asymmetric boss with a radius of approximately 0.046" and extends approximately 0.060" beyond the end face 190 of the bit engaging socket 176. In this configuration, the pin 188 is suitably configured to serve as a driving nib to engage the detent on the front sight of a firearm (e.g., a AR/15/M16/M4 family rifle, a AR-10/SR-25 family rifle, etc) to allow for front sight installation, removal, or adjustment, to remove the floor plate of a standard military magazine, and/or to remove the spring clevis in a bolt carrier. To protect the pin 188 when the main tool 104 is disposed within central passage 106 of the torque handle 102, various means can be employed. One such means is a protective insert 192 configured for being mounted within bit receiving passage 180 and having a shoulder 199 with a pin clearance (e.g., cut-out in which the pin is positioned when the protective insert 192 is mounted within bit receiving passage 180). Another such means is a circular recess formed in the floor of the central passage 106 of the torque handle body 107, thereby allowing the pin 188 to be positioned within the circular recess when the main tool 104 is disposed within central passage 106 of the torque handle 102.

Referring to FIG. 6, a threaded hole 193 is provided in a side face of the second tool body structure 152 at its first end portion 164. The threaded hole 195 extends substantially normal to the longitudinal centerline axis L of the main body 104. In this regard, the threaded hole 193 can be specifically configured to have a cleaning rod threadedly engaged therewith thereby allowing the main tool 104 to serve as a Tee handle for the cleaning rod.

Referring to FIG. 7, an end face 194 at the first end portion 164 of the second tool body structure 152 includes a plurality of elongated cavities 196 (e.g., punch receiving recesses) therein. An article such as, for example, a punch can be stored in each one of the elongated cavities 196. Diameter, cross-sectional shape, and/or depth of each one of the elongated cavities 196 can be configured dependent upon a respective article intended to be stored therein. It is disclosed herein that elongated cavities can be provided in an end face at the second end portion 156 of the first tool body structure 150.

It is disclosed herein that magnets can be used for retaining certain discrete tool elements in position with respect to the torque handle 102 and/or the main tool 104. With regard to the torque handle 102, one of more magnets can be used for securing contents (e.g., bits, punches, spare firearm parts, etc) within the bit receiving pockets 146. With regard to the main tool 104, one or more magnets can be used for securing contents within the central passage 163 of the boss 161, within the bit receiving passage 180, and/or within the punch receiving recesses 196.

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A multi-purpose firearm servicing tool, comprising
a tool body having a first end portion and a second end portion, wherein a longitudinal centerline axis of the tool body extends through the first and second end portions of the tool body; and
a plurality of tool elements each integral with a side face of the tool body at a respective position between the first and second end portions of the tool body, wherein each one of said tool elements provides a respective firearm servicing functionality; and
a gas tube clamp at a position between the first tool body structure and the second tool body structure, wherein opposing tube clamp surfaces of the gas tube clamp are selectively movable between a tube clamping configuration and a tube receiving configuration;
wherein the tool body includes a first tool body structure and a second tool body structure;
wherein the first tool body structure has a first threaded tool body interface at a first end portion thereof extending along the longitudinal centerline axis;
wherein the second tool body structure has a second threaded tool body structure interface at a first end portion thereof extending along the longitudinal centerline axis; and
wherein the second threaded tool body interface is threadedly engaged with the first threaded tool body interface for causing the second tool body structure to be longitudinally displaced with respect to the first tool body structure in response to relative rotational displacement therebetween.

2. The multi-purpose firearm servicing tool of claim 1 wherein at least one of said tool body structures has at least one punch receiving recess within an end face at the first end portion thereof.

3. The multi-purpose firearm servicing tool of claim 1 wherein:
a first one of said tool elements integral with the side face of the tool body is a rear sight windage wheel rotating tool element; and
a second one of said tool elements integral with the side face of the tool body is a thumb screw slot engaging tool element.

4. The multi-purpose firearm servicing tool of claim 1, further comprising:
a rear sight windage wheel rotating tool element integral with a side face of the tool body.

5. A multi-purpose firearm servicing tool, comprising:
an elongated tool body having a first end portion and a second end portion,
a gas tube clamp at a position between the first and second end portions of the elongated tool body, wherein opposing tube clamp surfaces of the gas tube clamp are selectively movable between a tube clamping configuration and a tube receiving configuration; and
a pin fixedly attached to the tool body at the first end portion thereof
wherein the elongated tool body includes a first tool body structure and a second tool body structure;
wherein the first tool body structure has a first threaded tool body interface at a first end portion thereof extending along the longitudinal centerline axis;
wherein the second tool body structure has a second threaded tool body structure interface at a first end portion thereof extending along the longitudinal centerline axis; and
wherein the second threaded tool body interface is threadedly engaged with the first threaded tool body interface for causing the second tool body structure to be longitudinally displaced with respect to the first tool body structure in response to relative rotational displacement therebetween.

6. The multi-purpose firearm servicing tool of claim 5 wherein:
at least one of said tool body structures has at least one punch receiving recess within an end face at the first end portion thereof; and
an end face at the first end portion of one of said tool body structures defines a contoured gas tube receiving surface of the gas tube clamp in which a gas tube of a firearm can be clamped as the first tool body structure is threadedly engaged with the second tool body structure.

7. A multi-purpose firearm servicing tool, comprising:
a tool body including a first tool body structure and a second tool body structure, wherein the first tool body structure has a first threaded tool body interface at a first end portion thereof extending along a longitudinal centerline axis thereof, wherein the second tool body structure has a second threaded tool body structure interface at a first end portion thereof extending along a longitudinal centerline axis thereof, wherein the second threaded tool body interface is threadedly engaged with the first threaded tool body interface for causing the second tool body structure to be longitudinally displaced with respect to the first tool body structure in response to relative rotational displacement therebetween;

a gas tube clamp at a position between the first tool body structure and the second tool body structure, wherein opposing tube clamp surfaces of the gas tube clamp are selectively movable between a tube clamping configuration and a tube receiving configuration; and a torque handle body having a tool body receiving cavity accessible through an opening at an end face at a first end portion thereof, wherein said first and second tool body structures are stowable within the tool body receiving cavity, and wherein the torque handle body and the tool body each include respective means for allowing the tool body to be coupled to the torque handle body for allowing a rotational torque to be applied to the tool body through rotation of the torque handle body.

8. The multi-purpose firearm servicing tool of claim 7 wherein
the first tool body structure includes a thumb screw slot engaging tool element integral with a side face thereof; and
the second tool body structure includes a rear sight windage wheel rotating tool element integral with a side face thereof.

9. The multi-purpose firearm servicing tool of claim 7 wherein at least one of said tool body structures has at least one punch receiving recesses within an end face at the first end portion thereof.

10. The multi-purpose firearm servicing tool of claim 7, further comprising:
a buffer tube nut receiving socket provided at the first end portion of the torque handle body.

11. The multi-purpose firearm servicing tool of claim 10 wherein
the first tool body structure includes a thumb screw slot engaging tool element integral with a side face thereof; and
the second tool body structure includes a rear sight windage wheel rotating tool element integral with a side face thereof.

12. The multi-purpose firearm servicing tool of claim 10 wherein at least one of said tool body structures has at least one punch receiving recesses within an end face at the first end portion thereof.

* * * * *